US008809398B2

(12) United States Patent
Köpsel et al.

(10) Patent No.: US 8,809,398 B2
(45) Date of Patent: Aug. 19, 2014

(54) LIQUID FORMULATIONS CONTAINING A CAROTINOID

(75) Inventors: Christian Köpsel, Weinheim (DE); Jesper Feldthusen Jensen, Nieder-Olm (DE)

(73) Assignee: BASF SE (DE)

( * ) Notice: Subject to any disclaimer, the term of this patent is extended or adjusted under 35 U.S.C. 154(b) by 721 days.

(21) Appl. No.: 12/522,554

(22) PCT Filed: Jan. 15, 2008

(86) PCT No.: PCT/EP2008/050401
§ 371 (c)(1),
(2), (4) Date: Jul. 9, 2009

(87) PCT Pub. No.: WO2008/087140
PCT Pub. Date: Jul. 24, 2008

(65) Prior Publication Data
US 2010/0120922 A1    May 13, 2010

(30) Foreign Application Priority Data

Jan. 16, 2007  (EP) .................................. 07100633
Mar. 30, 2007  (EP) .................................. 07105349

(51) Int. Cl.
| A61K 31/12 | (2006.01) |
| A61K 31/122 | (2006.01) |
| A61K 31/045 | (2006.01) |
| A61K 31/047 | (2006.01) |
| A61K 31/015 | (2006.01) |
| A61K 47/00 | (2006.01) |

(52) U.S. Cl.
USPC ............ 514/691; 514/729; 514/763; 514/772

(58) Field of Classification Search
None
See application file for complete search history.

(56) References Cited

U.S. PATENT DOCUMENTS

| 2,661,349 | A |   | 12/1953 | Caldwell |         |
|-----------|---|---|---------|----------|---------|
| 3,110,598 | A |   | 11/1963 | Müller et al. | |
| 4,522,743 | A |   | 6/1985  | Horn et al. | |
| 4,844,934 | A |   | 7/1989  | Lueddecke et al. | |
| 5,028,625 | A |   | 7/1991  | Motola et al. | |
| 5,078,980 | A |   | 1/1992  | Mullner et al. | |
| 5,350,773 | A |   | 9/1994  | Schweikert et al. | |
| 5,364,563 | A |   | 11/1994 | Cathrein et al. | |
| 5,637,618 | A |   | 6/1997  | Kurtz et al. | |
| 5,827,539 | A |   | 10/1998 | Gellenbeck | |
| 5,863,953 | A | * | 1/1999  | Luddecke et al. | 514/691 |
| 5,891,907 | A |   | 4/1999  | Kolter et al. | |
| 5,968,251 | A |   | 10/1999 | Auweter et al. | |
| 6,201,155 | B1 |  | 3/2001  | Burdet et al. | |
| 6,224,876 | B1 |  | 5/2001  | Kesharlal et al. | |
| 6,235,315 | B1 | * | 5/2001 | Runge et al. | 424/489 |
| 6,287,615 | B1 |  | 9/2001  | Runge et al. | |
| 6,639,113 | B2 |  | 10/2003 | Runge et al. | |
| 7,070,812 | B2 |  | 7/2006  | Runge et al. | |
| 2002/0110599 | A1 | | 8/2002 | Auweter et al. | |
| 2002/0128325 | A1 | | 9/2002 | Runge et al. | |
| 2002/0188019 | A1 | | 12/2002 | Ley et al. | |
| 2004/0033246 | A1 | * | 2/2004 | Naru et al. | 424/401 |
| 2005/0079223 | A1 | | 4/2005 | Estrella De Castro et al. | |
| 2005/0084462 | A1 | | 4/2005 | Klingenberg | |
| 2006/0035871 | A1 | * | 2/2006 | Auweter et al. | 514/169 |
| 2007/0054023 | A1 | | 3/2007 | Bingley | |
| 2008/0026124 | A1 | | 1/2008 | Musaeus et al. | |
| 2008/0113076 | A1 | | 5/2008 | Klingenberg | |
| 2008/0131515 | A1 | | 6/2008 | Ogawa et al. | |
| 2008/0193539 | A1 | | 8/2008 | Voelker | |
| 2008/0207775 | A1 | | 8/2008 | Musaeus et al. | |
| 2008/0220071 | A1 | * | 9/2008 | Jensen et al. | 424/489 |
| 2008/0248013 | A1 | | 10/2008 | Ikemoto et al. | |
| 2010/0028444 | A1 | | 2/2010 | Matuschek et al. | |
| 2010/0041607 | A1 | | 2/2010 | Jensen et al. | |
| 2010/0047426 | A1 | | 2/2010 | Matuschek et al. | |
| 2010/0120922 | A1 | | 5/2010 | Kopsel et al. | |
| 2010/0267838 | A1 | | 10/2010 | Kopsel | |
| 2011/0207831 | A1 | | 8/2011 | Kopsel | |

FOREIGN PATENT DOCUMENTS

| CA | 2210323 A1 | 8/1996 |
| CH | 418106 | 7/1966 |
| DE | 1211911 B | 3/1966 |
| DE | 3119383 A1 | 12/1982 |
| DE | 10059213 A1 | 6/2002 |
| DE | 10122898 A1 | 11/2002 |
| DE | 102004046026 A1 | 3/2006 |
| DE | 102005030952 A1 | 1/2007 |
| EP | 065193 A2 | 11/1982 |
| EP | 0065193 A2 | 11/1982 |
| EP | 0 239 086 A2 | 9/1987 |
| EP | 0410236 A2 | 1/1991 |

(Continued)

OTHER PUBLICATIONS

U.S. Appl. No. 12/522,558, filed Jul. 9, 2009, Jesper F. Jensen.
U.S. Appl. No. 12/443,237, filed Mar. 27, 2009, Matuschek et al.
U.S. Appl. No. 12/443,266, filed Mar. 27, 2009, Matuchek et al.
U.S. Appl. No. 12/522,558, filed Jul. 9, 2009, Jensen et al.
Manz, "Die anwendung und bedeutung von synthetischen carotinoiden in der lebens- und futtermittel-sowie in der pharmazeutischen industrie," Chimia, 1967, vol. 21, pp. 329-335.
U.S. Appl. No. 13/198,909, filed Aug. 5, 2011, Kopsel et al.

(Continued)

Primary Examiner — Sreeni Padmanabhan
Assistant Examiner — Jody Karol
(74) Attorney, Agent, or Firm — Drinker Biddle & Reath LLP

(57) ABSTRACT

The present invention relates to a liquid formulation containing at least one carotenoid, at least one hydrophilic protective colloid and at least one water-miscible alcohol. The formulation according to the invention can be added directly to aqueous or non-aqueous preparations. The invention compositions can be used in animal feed, human food or a dietary supplement and in pharmaceutical and cosmetic preparations.

8 Claims, No Drawings

(56) References Cited

FOREIGN PATENT DOCUMENTS

| | | |
|---|---|---|
| EP | 0416236 A2 | 3/1991 |
| EP | 0 551 638 A1 | 7/1993 |
| EP | 0732064 A1 | 9/1996 |
| EP | 0800825 A1 | 10/1997 |
| EP | 0832569 A2 | 4/1998 |
| EP | 0848913 A2 | 6/1998 |
| EP | 937412 A1 | 8/1999 |
| EP | 0978508 A2 | 2/2000 |
| EP | 1213013 A2 | 6/2002 |
| EP | 1219292 A1 | 7/2002 |
| EP | 1228705 A2 | 8/2002 |
| EP | 1 258 200 A2 | 11/2002 |
| EP | 1300394 B1 | 2/2004 |
| EP | 1460060 | 9/2004 |
| EP | 1 875 814 A1 | 1/2008 |
| EP | 1 927 287 A1 | 6/2008 |
| EP | 1952845 A1 | 8/2008 |
| GB | 970363 A | 9/1964 |
| JP | 63137657 A | 6/1988 |
| JP | 2025428 A | 1/1990 |
| JP | 4-262758 A | 9/1992 |
| JP | 7-99924 A | 4/1995 |
| JP | 7-083684 B2 | 9/1995 |
| JP | 2001226293 A | 8/2001 |
| JP | 2004-196673 A | 7/2004 |
| WO | WO-91/06292 A1 | 5/1991 |
| WO | WO-93/04598 A1 | 3/1993 |
| WO | WO-94/19411 A1 | 9/1994 |
| WO | WO-96/13178 A1 | 5/1996 |
| WO | WO-96/23420 A1 | 8/1996 |
| WO | WO-96/23429 A1 | 8/1996 |
| WO | WO-03/017785 A1 | 3/2003 |
| WO | WO-03/066583 A1 | 8/2003 |
| WO | WO-03/086293 A2 | 10/2003 |
| WO | WO-03/102116 A2 | 12/2003 |
| WO | WO-2004/084862 A1 | 10/2004 |
| WO | WO-2005/060923 A1 | 7/2005 |
| WO | WO 2005060923 A1 * | 7/2005 |
| WO | WO-2006/022187 A1 | 3/2006 |
| WO | WO-2006/125591 A1 | 11/2006 |
| WO | WO-2007/003543 A1 | 1/2007 |
| WO | WO-2007/009601 A1 | 1/2007 |
| WO | WO 2007003598 A1 * | 1/2007 |
| WO | WO-2007/020057 A1 | 2/2007 |
| WO | WO-2007/045488 A1 | 4/2007 |
| WO | WO 2008/087090 | 7/2008 |
| WO | WO-2008/087090 A1 | 7/2008 |
| WO | WO2008/087139 | 7/2008 |
| WO | WO-2008/087139 A2 | 7/2008 |
| WO | WO-2008/087140 A2 | 7/2008 |
| WO | WO 2009/027499 | 3/2009 |
| WO | WO-2009/027499 A2 | 3/2009 |
| WO | WO-2009/068432 A1 | 6/2009 |
| WO | WO-2010/040683 A1 | 4/2010 |
| WO | WO-2010/100226 A1 | 9/2010 |
| WO | WO-2010/100227 A1 | 9/2010 |
| WO | WO-2010/100228 A1 | 9/2010 |
| WO | WO-2010/100229 A1 | 9/2010 |
| WO | WO-2010/100232 A2 | 9/2010 |
| WO | WO-2010/100233 A1 | 9/2010 |
| WO | WO-2010/112406 A1 | 10/2010 |

OTHER PUBLICATIONS

Bai, Y., Doctoral Thesis "Preparation and Structure of Octenyl Succinic Anhydride Modified Waxy Maize Starch, Microporous Starch and Maltodextrin," Department of Grain Science and Industry, College of Agriculture, Kansas State University, Manhattan, Kansas, 2008.

Drusch, S., et al., "Impact of Physicochemical Characteristics on the Oxidative Stability of Fish Oil Microencapsulated by Spray-Drying," J. Agric. Food Chem. 2007, vol. 55, pp. 11044-11051.

Ley, Jakob P., et al., New Bitter-Masking Compounds: Hydroxylated Benzoic Acid Amides of Aromatic Amines as Structural Analogues of Homeriodictyol, 2006, Journal of Agricultural and Food Chemistry, vol. 54, No. 22, pp. 8574-8579.

Manz, V.U., "Die anwendung und bedeutung von synthetischen carotinoiden in der lebens- und futtermittel-sowie in der pharmazeutischen industrie," Chimia, 1967, vol. 21, pp. 329-335.

Roy, G.M., Modifying Bitterness: Mechanism, Ingredients, and Applications, Apr. 29, 1997, CRC Press.

BASF Brochure, "Products for the Dietary Supplement, Beverage and Food Industries—Techinical Information", (2005), p. 4-5, 181-185.

Research Disclosure No. 170064, "Herstellung neuer Anwendungsformen von Carotinoidfarbstoffen mittels Ultramikronisierung", vol. 170, No. 6, (1978), p. 51.

Research Disclosure No. 452072, "Production of high load carotenoid product forms with modified food starch", vol. 452, No. 12, (2001), p. 2052.

* cited by examiner

LIQUID FORMULATIONS CONTAINING A CAROTINOID

CROSS-REFERENCE TO RELATED APPLICATIONS

This application is a national stage application (under 35 U.S.C. §371) of PCT/EP2008/050401, filed Jan. 15, 2008, which claims benefit of European application 07100633.2, filed Jan. 16, 2007 and European application 07105349.0 filed Mar. 30, 2007.

BACKGROUND OF THE INVENTION

The present invention relates to liquid formulations, method for their production, and their use as addition to animal feeds and human foods.

The formulation of carotenoids represents a particular challenge because of their slight solubility in water and their chemical instability. There have thus been numerous attempts to provide carotenoid formulations which, on the one hand, are stable and, on the other hand, show good bioavailability and provide the desired color yield on use. Liquid carotenoid formulations are of particular interest because the obtaining of the carotenoids in powder form and the preparation of a liquid formulation by the user become superfluous.

Production of carotenoid primary particles with a particle size in the nanometer range is crucial for achieving adequate bioavailability and color yields. In order to produce such particles, grinding processes have been used in the prior art, as described for example in WO 91/06292 and WO 94/19411. The carotenoids are ground using a colloid mill in aqueous or oily media, achieving a particle size in the nanometer range.

EP 1 460 060 A describes the production of lutein suspensions by grinding in an oil. It also describes cold water-dispersible lutein formulations which are produced by dissolving lutein in a water-immiscible organic solvent and encapsulating in modified starch in the presence of an emulsifier.

US 2005/0084462 describes the production of a color mixture for use in food products, pharmaceutical and cosmetic products by grinding a color in water in the presence of gum arabic as carrier and subsequent heating to 30 to 60° C.

U.S. Pat. No. 5,827,539 describes the grinding of a dispersion of a carotenoid in oil, forming an emulsion with a mixture of starch, sugar and an antioxidant, and subsequent spray drying.

WO 9613178 describes the production of stable lycopene concentrates by grinding lycopene in a liquid medium in which the lycopene is substantially insoluble. The liquid medium used is glycerol, propylene glycol or ethanol. However, a hydrocolloid is not employed.

WO 96/23420 describes the production of oily astaxanthin suspensions with particle sizes of <2 µm by grinding astaxanthin, adding an oil during or after the grinding. The use of protective colloids or emulsifiers is not disclosed. It is pointed out that the particles are prone to agglomeration. Accordingly, further stabilization by storing the suspension below the solidification temperature is considered.

WO 93/04598 describes the production of a carotenoid composition comprising a carotenoid in an oil, a dispersion of a water-dispersible matrix former, for example a sugar, and of a stabilizer, for example gelatin or casein, and an emulsifier and, where appropriate, a non-oily solvent such as glycerol.

BRIEF SUMMARY OF THE INVENTION

The invention is relates to a liquid formulation comprising at least one carotenoid, at least one hydrophilic protective colloid and at least one water-miscible alcohol.

The present invention is based on the object of providing a liquid carotenoid formulation which can easily be produced and can be employed by the user without additional effort.

It has now surprisingly been found that this object is achieved with a liquid formulation which, besides a carotenoid and a hydrophilic protective colloid, comprises at least one water-miscible alcohol.

DETAILED DESCRIPTION OF THE INVENTION

The present invention therefore relates to a liquid formulation comprising at least one carotenoid, at least one hydrophilic protective colloid and at least one water-miscible alcohol.

Carotenoids which can be employed are the known representatives which can be obtained from natural sources or by synthesis. It is moreover possible to employ the known representatives which can be obtained from natural sources or by synthesis. Examples thereof are β-carotene, lycopene, lutein, astaxanthin, zeaxanthin, cryptoxanthin, citranaxanthin, canthaxanthin, echinenone, bixin, β-apo-4-carotenal, β-apo-8-carotenal, β-apo-4-carotenoic esters, singly or as mixture. Astaxanthin, β-carotene, β-apo-8-carotenal, ethyl β-apo-8'-carotenoate, canthaxanthin, citranaxanthin, echinenone, lutein, lycopene and zeaxanthin are preferred. Astaxanthin and canthaxanthin, and especially astaxanthin, are particularly preferred.

The carotenoids generally have a particle size in the range from 50 nm to 10 µm, preferably 100 nm to 5 µm, particularly preferably 100 nm to 3 µm, 150 nm to 2 µm and especially 200 nm to 1 µm.

Water-soluble or -swellable colloids are suitable as hydrophilic protective colloid. The protective colloids are preferably protein-based, modified starch derivatives and modified cellulose derivatives. Protein-based protective colloids are in particular casein, caseinate, bovine, porcine or fish gelatin, especially acid- or base-degraded gelatin having Bloom numbers in the range from 0 to 250, and mixtures thereof. The modified starch derivatives and cellulose derivatives are in particular the esters, for example starch octenylsuccinate. Corresponding products are commercially available under the name Purity Gum 2000 from National Starch or Clear Gum CO 01 from Roquette, Hi Cap 100 or Capsul from National Starch.

Modified starches are preferably used as hydrophilic protective colloid.

Suitable water-miscible alcohols are monoalcohols and polyalcohols. The monoalcohols are alkanols such as methanol, ethanol, isopropanol etc. However, polyalcohols are preferably used. These are in particular dihydric or trihydric alcohols. Examples thereof are glycol, propylene glycol, butylene glycol, polyethylene glycol, polypropylene glycol, glycerol, monoesters of glycerol with $C_1$-$C_5$ monocarboxylic acids, or monoethers of glycerol. The formulations of the invention particularly preferably comprise glycerol.

The carotenoids are generally present in the formulations of the invention in an amount in the range from 0.1 to 50% by weight, preferably 0.2 to 30% by weight and especially 1.0 to 15% by weight based on the total weight of the formulation.

The amount of hydrophilic protective colloid is generally in the range from 1 to 40% by weight, preferably 2 to 30% by weight and in particular 3 to 25% by weight.

The ratio of carotenoid to hydrophilic protective colloid is generally in the range from 5:1 to 1:5, preferably 3:1 to 1:3, by weight. The amount of water-miscible alcohols is generally in the range from 30 to 95% by weight, in particular 30 to 90% by weight and particularly preferably 35 to 90% by weight, based on the total weight of the formulation.

The formulations of the invention may comprise water in an amount of up to 40% by weight, preferably up to 35% by weight, based on the total weight of the formulation.

The formulations of the invention preferably comprise no oil.

To increase the stability of the active ingredient in relation to oxidative degradation, it is advantageous to add stabilizers such as α-tocopherol, t-butylhydroxytoluene, t-butylhydroxyanisole, ascorbic acid or ethoxyquin.

The formulations of the invention may additionally comprise ancillary substances such as thickeners, hard fats, chelating agents, for example alkali metal or alkaline earth metal salts of citric acid, phythic acid or phosphoric acid and/or emulsifiers. Examples of emulsifiers are ascorbyl palmitate, polyglycerol fatty acid esters such as polyglycerol 3 polyricinoleate (PGPR 90), sorbitan fatty acid esters such as sorbitan monostearate (span 60), PEG(20) sorbitol monooleate, propylene glycol fatty acid esters or phospholipids such as lecithin.

The formulations of the invention are produced by grinding a dispersion of the carotenoid and of the hydrophilic protective colloid in the water-miscible alcohol used. It is also possible, however, to add part of the alcohol during the grinding. The grinding is continued until an average particle size of the carotenoid crystals and of the hydrophilic protective colloid of <5 μm, preferably <1 μm, is reached. It is possible to employ as grinding apparatus the usual apparatuses known to the skilled worker, for example colloid mills, ball mills such as Dynomill of the KDL or multilab type.

The formulations of the invention can be added directly to aqueous or nonaqueous preparations. They can, however, also be diluted further with the alcohol used before the addition.

The formulations are suitable inter alia as additive to animal feeds and human food preparations or compound feed, as compositions for producing pharmaceutical and cosmetic preparations, and for producing dietary supplement products in the human and animal sector. The suspensions can preferably be employed as addition to feed in livestock nutrition, for example by mixing into feed pellets on extrusion or by application or spraying onto feed pellets. Use as addition to feed takes place in particular by direct spraying on of the formulations of the invention, for example as so-called post-pelleting application. The feed pellets are preferably loaded with the formulations under reduced pressure.

Typical areas of use in the human food sector are for example the vitaminization and coloring of beverages, dairy products such as yoghurt, milk drinks or milk ice, and blancmange powders, egg products, baking mixes and confectionery. In the cosmetics sector, the oily suspensions can be used for example for decorative personal care compositions, for example in the form of a cream, of a lotion, as lipstick or makeup.

The invention further relates to dietary supplements, animal feeds, human foods and pharmaceutical and cosmetic preparations which comprise the formulations of the invention. Preference is given to animal feeds, especially feed pellets, loaded with the formulations.

Dietary supplement products and pharmaceutical preparations mean inter alia tablets, coated tablets and, preferably, hard and soft gelatin capsules which comprise the formulations of the invention.

The following examples illustrate the invention without limiting it.

Example 1

Production of a 10.5% Strength β-Carotene Dispersion 784.16 g of glycerol were introduced into a 2 l glass beaker and 110.84 g ($H_2O$ content 5.27%) of Purity Gum 2000 (octenylsuccinate-starch) were stirred in. Subsequently, 105.0 g of crystalline β-carotene were stirred in until it was completely wetted (30 to 40 min). The dispersion obtained in this way was then ground with a Dynomill Multilab using SiLi beads Zr beads stabilized with yttrium and with a diameter of 0.4 to 0.6 mm from Siegmund Lindner. The grinding container was charged with 400 ml of these grinding beads. The grinding took place at a temperature in the range from 54 to 70° C., a grinding slit of 0.10 mm and with the mill revolving at 2986 rpm.

Example 2

Production of a 7.0% Strength β-Carotene Dispersion

A dispersion of 210.0 g of crystalline β-carotene, 221.68 g of Purity Gum 2000 ($H_2O$ content 5.27%) and 2568.32 g of glycerol was ground by the method described in example 1. The grinding took place at a temperature in the range from 52 to 68° C. After 1.5 h, a low-viscosity dispersion in which the β-carotene had a particle size of 438 nm was obtained.

We claim:

1. A liquid formulation comprising at least one carotenoid, starch octenylsuccinate, and glycerol, wherein the average particle size of the carotenoid and starch octenylsuccinate is less than 5 μm and wherein the carotenoid is present in an amount of 1.0 to 15% by weight based on the total weight of the formulation, the liquid formulation comprising no oil, wherein the glycerol is present in an amount of 30 to 95% by weight based on the total weight of the formulation.

2. The formulation according to claim 1, wherein the carotenoid is astaxanthin.

3. An animal feed, human food or dietary supplement comprising the formulation according to claim 1.

4. A pharmaceutical preparation comprising the formulation according to claim 1.

5. A cosmetic preparation comprising the formulation according to claim 1.

6. The formulation according to claim 1, wherein the carotenoid is selected from β-carotene, lycopene, lutein, astaxanthin, zeaxanthin, cryptoxanthin, citranaxanthin, canthaxanthin, echinenone, bixin, β-apo-8-carotenal, β-apo-4-carotenoic esters, and mixtures thereof.

7. The formulation according to claim 1, wherein the formulation comprises water in an amount of up to 40% by weight, based on the total weight of the formulation.

8. The formulation according to claim 1, wherein the formulation comprises water in an amount of up to 35% by weight, based on the total weight of the formulation.

* * * * *